(12) United States Patent
DeRoos et al.

(10) Patent No.: US 7,555,934 B2
(45) Date of Patent: Jul. 7, 2009

(54) FLUID PERMEATION TESTING APPARATUS EMPLOYING MASS SPECTROMETRY

(75) Inventors: Fred L. DeRoos, Woodbury, MN (US); Mark E. Mueller, Marine-on-the-St. Croix, MN (US); Mark A. Roehrig, Stillwater, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 239 days.

(21) Appl. No.: 11/470,766

(22) Filed: Sep. 7, 2006

(65) Prior Publication Data

US 2008/0060418 A1    Mar. 13, 2008

(51) Int. Cl.
*G01N 15/08* (2006.01)
(52) U.S. Cl. .......................................................... 73/38
(58) Field of Classification Search ...................... 73/38, 73/40.7, 46, 865.6, 865.8, 866
See application file for complete search history.

(56) References Cited

U.S. PATENT DOCUMENTS

| | | | |
|---|---|---|---|
| 3,286,509 A * | 11/1966 | Gluckman et al. ............. | 73/38 |
| 3,545,931 A | 12/1970 | McKinley, Jr. | |
| 3,590,634 A | 7/1971 | Pasternak | |
| 3,604,246 A | 9/1971 | Toren | |
| 3,618,361 A * | 11/1971 | Stephens et al. ................ | 73/38 |
| 3,718,434 A | 2/1973 | Pierce | |
| 3,926,561 A | 12/1975 | Lucero | |
| 4,201,913 A | 5/1980 | Bursack et al. | |
| 4,855,594 A | 8/1989 | Kimock et al. | |
| 4,944,180 A | 7/1990 | Tou et al. | |
| 5,054,328 A | 10/1991 | Long et al. | |
| 5,159,829 A | 11/1992 | Mayer et al. | |
| 5,311,016 A | 5/1994 | Villa-Aleman | |
| 5,361,625 A | 11/1994 | Ylvisaker | |
| 5,390,539 A | 2/1995 | Mayer | |
| 5,591,898 A | 1/1997 | Mayer | |
| 5,817,924 A | 10/1998 | Tuomela et al. | |
| 6,009,743 A | 1/2000 | Mayer | |
| 6,413,645 B1 | 7/2002 | Graff et al. | |
| 6,492,043 B1 * | 12/2002 | Knights et al. ................ | 429/13 |
| 6,640,615 B1 | 11/2003 | Morrow | |
| 6,766,682 B2 | 7/2004 | Engle et al. | |
| 6,793,994 B2 | 9/2004 | Tsai et al. | |

(Continued)

OTHER PUBLICATIONS

M. R. Keenan and J. E. Reich, "A Mass Spectrometer Based Gas Permeation Apparatus", Sandia National Labs, Albuquerque, NM, Apr. 1985, pp. 3-31.

(Continued)

*Primary Examiner*—John Fitzgerald
(74) *Attorney, Agent, or Firm*—Daniel R. Pastirik

(57) ABSTRACT

A fluid permeation testing apparatus provides for filling a first cavity of a test cell with a test fluid and filling a second cavity of the test cell with a challenge fluid. The challenge fluid comprises at least one analyte useful for testing permeation of the challenge fluid through a test film that separates the first and second cavities. Samples of the test fluid in the first cavity are introduced to a mass spectrometer, such as in a pulsed manner, without substantially changing the total pressure in first cavity. Samples of the test fluid in the first cavity may be introduced to the mass spectrometer while maintaining substantially balanced total pressures in the first and second cavities.

37 Claims, 7 Drawing Sheets

U.S. PATENT DOCUMENTS

| | | |
|---|---|---|
| 6,804,989 B2 | 10/2004 | Bujas et al. |
| 6,851,316 B2 | 2/2005 | Micke et al. |
| 6,892,567 B1 | 5/2005 | Morrow |
| 7,257,990 B2 | 8/2007 | Bujas et al. |
| 2002/0162384 A1 | 11/2002 | Sharp et al. |
| 2003/0074954 A1 | 4/2003 | Engle et al. |
| 2004/0123646 A1 | 7/2004 | Echigo et al. |
| 2008/0060418 A1* | 3/2008 | DeRoos et al. ............... 73/38 |
| 2008/0105038 A1 | 5/2008 | Jons et al. |

OTHER PUBLICATIONS

I. E. Sodal and D. A. Hanna, "Improved Mass Spectrometer Measurements Using a Pulsed Gas Sampling System", J. Vac. Sci. Technol. A 15(1), Jan./Feb. 1997, pp. 176-181.

* cited by examiner

FLUID PERMEATION TESTING APPARATUS EMPLOYING MASS SPECTROMETRY

FIELD OF THE INVENTION

The present invention relates to apparatuses for testing fluid permeability of films, such films including barrier films and ultra-low permeability films.

BACKGROUND

Flexible polymer substrates are being developed that incorporate optical and electronic elements. Organic light emitting diodes (OLEDs) and transistor-based electronics are examples of such elements that can be fabricated on flexible polymer substrates. Polymer substrates are attractive due to their being lightweight, impact resistant, and flexible. However, polymer substrates typically have poor barrier properties, making devices fabricated on such substrates vulnerable to oxygen and moisture ingression.

Due to the low barrier performance of polymeric material to moisture and oxygen, polymer substrates need to be protected with a barrier film. As the performance of low permeability barrier films increases, improved techniques are needed to accurately measure relatively low gas and moisture permeation rates for barrier coated polymer substrates.

SUMMARY OF THE INVENTION

The present invention is directed to apparatuses for fluid permeation testing. According to embodiments of the present invention, a permeation testing apparatus includes a mass spectrometer fluidly coupled to a test cell apparatus. A controller, communicatively coupled to the test cell apparatus, coordinates filling a first cavity of a test cell with a test fluid and filling a second cavity of the test cell with a challenge fluid. The challenge fluid preferably comprises at least one analyte useful for testing permeation of the challenge fluid through a test film that separates the first and second cavities. Samples of the test fluid from the first cavity are introduced to the mass spectrometer, such as in a pulsed manner.

Presence of the analyte indicative of challenge fluid permeation through the test film is detected using the mass spectrometer. A rate of permeation of the challenge fluid through the test film may be determined using data produced by the mass spectrometer, such as by the controller or other processing device. Apparatuses implemented in accordance with the present invention are particularly useful for fluid permeation testing of low permeability films, such as ultra-low permeability films.

According to one approach, samples of the test fluid from the first cavity are introduced to a mass spectrometer without substantially changing a total pressure in the first cavity. According to another approach, samples of the test fluid in the first cavity are introduced to the mass spectrometer while maintaining substantially balanced total pressures in the first and second cavities.

In accordance with embodiments of the present invention, a permeation testing apparatus includes a mass spectrometer and a controllable valve having an inlet and an outlet, the outlet coupled to the mass spectrometer. The apparatus further includes a test cell comprising a first cavity, a second cavity, and a support arrangement. A first port arrangement is configured to facilitate fluid communication between the first cavity and a test fluid source and between the first cavity and the inlet of the controllable valve. A second port arrangement is configured to facilitate fluid communication between the second cavity and a challenge fluid source containing a challenge fluid.

The support arrangement is configured to suspend a test film between the first and second cavities. A pressure sensing arrangement is configured to sense total pressures in the first and second cavities. The controller is coupled to the controllable valve.

According to one configuration, the controller is configured to controllably actuate the valve to deliver samples of a test fluid in the first cavity to the mass spectrometer without substantially changing a total pressure in the first cavity. According to another configuration, the controller is configured to controllably actuate the valve to deliver samples of a test fluid in the first cavity to the mass spectrometer while substantially balanced total pressures are maintained in the first and second cavities.

The controllable valve may include a solenoid-actuated sampling valve. The controllable valve may be configured to pulsedly sample a negligible volume of test fluid from the first cavity, such as less than about 10 microliters (e.g., 1 to 1,000 picoliters). The controllable valve may be controlled by a computer-controlled high voltage pulse generator that generates a control signal for controlling the state of the valve. A processor of, or coupled to, the testing apparatus (e.g., on-board the controller or external thereof) may be configured to determine a rate of permeation of the challenge fluid through the test film using data produced by the mass spectrometer.

The support arrangement includes a gasket arrangement provided at respective ends of the test film. In this configuration, the gasket arrangement and test film define a seal between the first and second cavities. The gasket arrangement may include metal gaskets provided above and below respective end surfaces of the test film. In an alternative, configuration, the gaskets may be adhesively mounted above and below the respective end surfaces of the test film. An additional sealing arrangement may be provided peripheral to the gasket arrangement, and a third port arrangement may be provided that extends from a location between the sealing and gasket arrangements to an exterior surface of the test cell.

The test fluids may be gases and challenge fluids may be gases or liquids. The test fluid may be an inert gas, such as nitrogen. The challenge fluid, for example, may comprise an inert gas, such as nitrogen, and a challenge gas or vapor. The challenge fluid may comprise an analyte such as oxygen, water, or an isotope of an element. The challenge fluid may comprise two or more analytes. Each of the analytes may be detected using the mass spectrometer. The analytes may be detected sequentially or concurrently by the mass spectrometer. Detecting presence of the one or more analytes may involve using a selected ion monitoring technique. A rate of permeation of the challenge fluid through the test film may be determined using data produced by the mass spectrometer, such as by use of a processor or controller having a processing capability.

The total pressure in each of the first and second cavities may be atmospheric pressure or an absolute pressure above or below atmospheric pressure. The apparatus typically provides for controller concurrent pressure-balanced filling of the first and second cavities with the test and challenge fluids, respectively. The testing method may be performed at ambient temperature or other selected temperature. The temperature may be adjusted to perform an Arrhenius evaluation of the system, such as to validate Arrhenius assumptions.

A testing apparatus of the present invention may be configured to perform permeation testing of multiple test films using a single mass spectrometer. In such an arrangement, a test film is provided in each of a number of test cells, and each test cell is fluidly coupled to a common mass spectrometer. The challenge fluids associated with each of the test cells may comprise the same or different analyte(s).

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
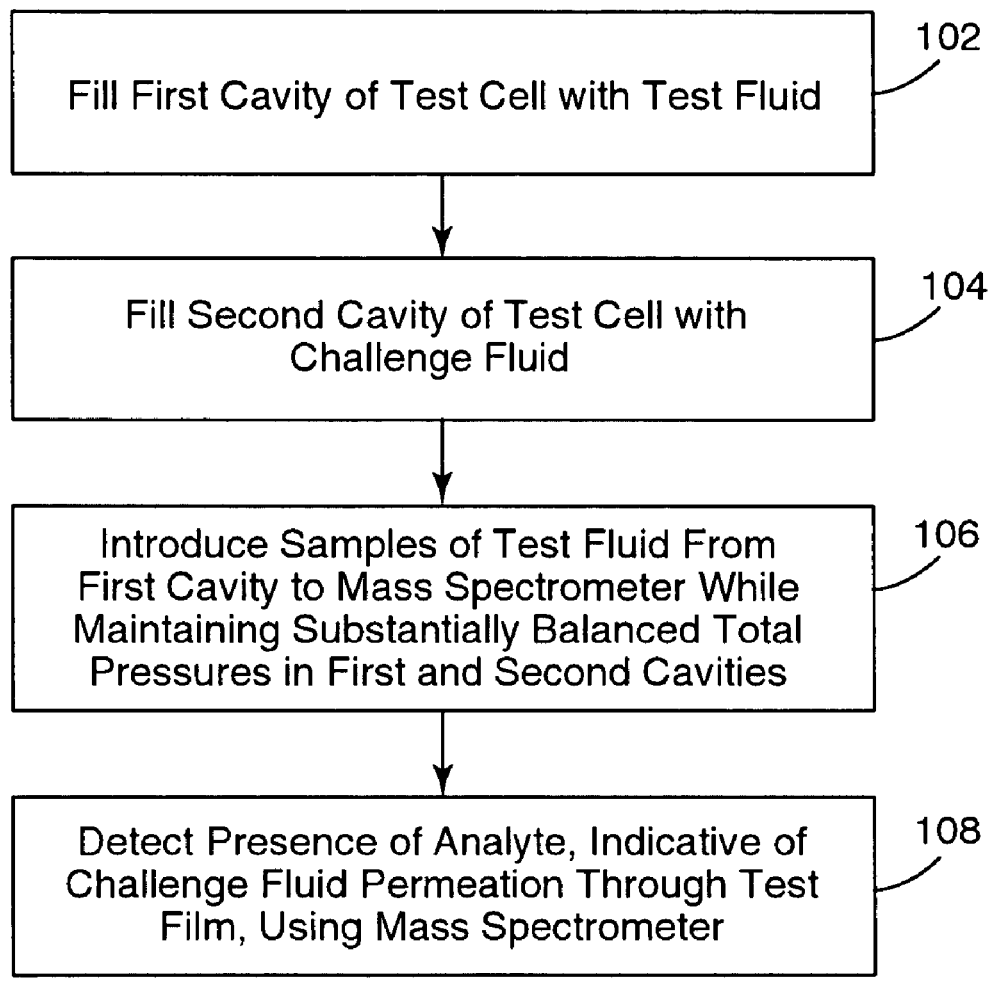
FIG. 1 is a flow diagram of a method of fluid permeation testing that may be implemented by a test apparatus in accordance with an embodiment of the present invention.

While the invention is amenable to various modifications and alternative forms, specifics thereof have been shown by way of example in the drawings and will be described in detail. It is to be understood, however, that the intention is not to limit the invention to the particular embodiments described. On the contrary, the intention is to cover all modifications, equivalents, and alternatives falling within the scope of the invention as defined by the appended claims.

DETAILED DESCRIPTION OF EMBODIMENTS

In the following description of the illustrated embodiments, reference is made to the accompanying drawings that form a part hereof, and in which is shown by way of illustration, various embodiments in which the invention may be practiced. It is to be understood that the embodiments may be utilized and structural changes may be made without departing from the scope of the present invention.

The present invention relates to apparatuses that provide for enhanced testing of fluid permeation through test films, such as barrier films and, in particular, ultra-low permeability films. The term ultra-low permeability refers to permeability of less than about 0.005 grams per square meter per day for water and less than about 0.005 cc per square meter per day for oxygen (noting that cc and g are interchangeable by using a factor of 22,400 (cc.mol)/(mol.32 g) appropriately).

Fluid permeation testing apparatuses and techniques of the present invention provide an extremely sensitive and selective process for measuring permeation and the rate of permeation of a fluid through test films using mass spectrometry. The fluid may be a gas or a liquid. For example, apparatuses of the present invention may be implemented to detect permeation of oxygen, moisture or other gases and liquids through test films, and measure permeation rates for such gases and liquids.

A fluid permeation testing apparatus according to embodiments of the present invention may provide for substantially balanced total pressures on both sides of the test film. For example, the total pressures on both sides of the test film may be atmospheric pressures or pressures above or below atmospheric pressure. Preferably, the substantially balanced total pressure at which fluid permeability testing of a test film is conducted reflects the pressure of the environment in which the test film is intended to be used. The intended environment of use for a given test film is often an ambient environment having atmospheric pressure conditions. Other environments may be more hostile, such as the vacuum of space or high pressure under-water (e.g., deep sea) environments.

According to other embodiments, a testing apparatus of the present invention may provide for negligible changes in the total pressure on a test side of the test film during fluid permeation testing. The total pressure on the test side of the test film may be atmospheric pressure or a pressure above or below atmospheric pressure, such as a pressure of the environment in which the test film is intended to be used. According to these embodiments, the total pressures on both sides of the test film may be different or substantially balanced.

Temperature may similarly be selected, based on the actual intended use of the test film being tested. Moreover, the total pressure in the challenge and/or test cavities may be changed as desired to study the temperature dependency of permeation for test films and permeating analytes. Also, temperature may be adjusted to perform an Arrhenius evaluation of the system. For example, permeation testing in accordance with the present invention may be applied to validate Arrhenius assumptions. Temperature of the test cell may be controlled in a variety of ways, including placing the test cell(s) in a temperature controlled oven or provision of intra-cell thermal management, such as provision of heating/cooling lines or channels within the test cell(s).

Measuring fluid permeability of test films samples at ambient pressures and temperatures, for example, represents a substantial departure from traditional approaches of making permeation rate measurements on low permeability materials. Traditional mass spectroscopy-based permeation testing of low permeability materials typically involves use of a vacuum on the sampling side of the film being tested, and/or use of a higher total pressure of the challenge vapor on the other side of the test film. Also, conventional testing approaches typically require that the test film have one to several backing plates with many perforations to keep the test film from stretching or rupturing. There is much scientific speculation on how much effect the backing plates have on the permeability of challenge gases or vapors through the test films.

A fluid permeation testing approach of the present invention avoids these and other problems associated with traditional testing approaches, including eliminating altogether the need for backing plates. Significantly, provision of balanced total pressures on both sides of a test film or only negligibly changing the total pressure on the test side of the test film during sampling advantageously allows for direct measuring of permeation rates without having to apply mathematical corrections or modeling to measurements made under conditions differing from those of actual use.

According to embodiments of the present invention, fluid permeation testing involves use of a mass spectrometer using selected ion monitoring tuned for enhanced sensitivity at relatively low masses, and does not require use of radioactive isotopes. Oxygen and water molecules, for example, are quite low in mass compared to the typical mass/charge sensing range of a conventional mass spectrometer. Selective ion monitoring by the mass spectrometer that is optimally tuned for small molecules provides for an increase in the signal-to-noise ratio.

Fluid permeation testing according to embodiments of the present invention may involve a pulsed sample injection technique that provides for the delivery of a negligibly small amount of the test fluid from the test cavity to the mass spectrometer, and allows the test cavity to accumulate the permeating analyte. This effectively integrates the change in analyte concentration, but does not significantly change the total pressure on the test side of the test film or disrupt equilibrium of total pressures on both sides of the test film. A pulsed sample injection technique of the present invention improves discrimination between signal and background noise and provides a continuous measurement of signal (sample) and background (baseline). For example, pulsed sampling provides for baseline compensation for drift in the background of the mass spectrometer.

Further, an optimized ion source volume for the mass spectrometer may be employed, when needed or desired, to enhance the collection of ions generated from a given amount of a permeated analyte, such as oxygen or moisture, for example. Also, permeation testing of the present invention provides for measurement of a multiplicity of analytes, either sequentially or virtually simultaneously.

Fluid permeation testing techniques of the present invention may be used in a wide range of applications. One particularly useful application involves permeation testing of ultra-barrier films that are developed to protect, and extend the operating life of, organic integrated circuits from oxygen and moisture. For example, organic light emitting diodes and organic thin-film transistors are being developed to provide for less expensive, lighter weight, and flexible displays and electronics. Ultra-barrier films are needed that can protect such OLEDs and organic integrated circuits from moisture and oxygen to give them the desired lifetimes.

In order to develop such ultra-barrier films and to control their quality, it is essential to be able to measure very low oxygen and water permeability rates through these films. Useful measurement systems should be capable of measuring permeability of oxygen and moisture to a level lower than $10^{-5}$ grams of oxygen per square meter per day ($10^{-5}$ g/m$^2$/day). A fluid permeation testing approach according to the present invention may be implemented to measure oxygen permeation rates to a level of about $10^{-6}$ g/m$^2$/day to about $10^{-9}$ g/m$^2$/day. For example, fluid permeation testing in accordance with the present invention may be implemented to measure oxygen permeation rates through a test film in the range of about $10^{-6}$ g/m$^2$/day to about $10^{-9}$ g/m$^2$/day in a test period of about one to three days, assuming negligibly small lag times in this illustrative example.

As was previously discussed, measuring fluid permeability of test films samples at ambient pressures and temperatures represents a substantial departure from traditional testing approaches. Such traditional approaches do not allow for direct measuring of fluid permeation rates, but instead rely on mathematical corrections or modeling to account for accelerated permeation of the challenge fluid through the test film due to a large total pressure differential developed across the test film. The methods illustrated in FIGS. 1-3 advantageously allow for direct measuring of fluid permeation rates (at ambient or other conditions) without having to apply mathematical corrections or modeling to measurements made under conditions differing from those of actual or intended use.

Turning now to FIG. 1, there is illustrated a method of fluid permeation testing that may be implemented by a test apparatus in accordance with an embodiment of the present invention. According to the illustrative example shown in FIG. 1, a first cavity of a test cell is filled 102 with a test fluid. An appropriate test fluid is nitrogen gas or other inert gas, for example. A second cavity of the test cell is filled 104 with a challenge fluid. The first and second cavities are preferably filled concurrently. The challenge fluid typically comprises nitrogen or other inert gas that is used as the test fluid and an analyte of interest, such as oxygen. The analyte may also be an isotope of an element of the challenge fluid. For example, the challenge fluid may include a first isotope of oxygen (e.g., $^{16}$O) and the test fluid may include a second isotope of oxygen (e.g., $^{18}$O). Permeation characteristics of the challenge fluid through the test film may be determined based on detection of a third isotope of molecular oxygen that results from the combination of the first and second oxygen isotopes.

Substantially balanced total pressures are preferably maintained 106 in the first and second cavities during permeation testing. Samples of the test fluid in the first cavity are introduced 108 to a mass spectrometer, such as in a pulsed manner for example. Using the mass spectrometer, the presence of an analyte of the challenge fluid is detected 110, which is indicative of challenge fluid permeation through the test film.

Use of substantially balanced total pressures in the test and challenge fluid cavities of a test cell as described herein typically involves concurrent evacuation of the first and second cavities for the initial degassing of the test film. This approach typically involves concurrent pressure-balanced filling of the test and challenge cavities. The challenge cavity is typically filled with nitrogen (or other inert gas) along with the challenge fluid (gas, vapor, or liquid, such as water, oxygen or other challenge material). The test cavity, which is sampled to the mass spectrometer, is typically filled with pure nitrogen or other inert gas. Synchronized filling and pressure balancing of the test and challenge cavities of the test cell may be accomplished using a suitable pressure sensor and suitable fast switching valves, such as solenoid/pneumatic fast switching valves, specific implementations of which are described herein below.

In another method of fluid permeation testing that may be implemented by a test apparatus in accordance with another embodiment of the present invention, a first cavity of a test cell is filled with a test fluid, and a second cavity of the test cell is filled with a challenge fluid. The first and second cavities are preferably filled concurrently. Samples of the test fluid in the first cavity are introduced to a mass spectrometer, such as in a pulsed manner, without substantially changing the total pressure in the first cavity. Using the mass spectrometer, the presence of an analyte of the challenge fluid is detected, which is indicative of challenge fluid permeation through the test film.

Figure 2:
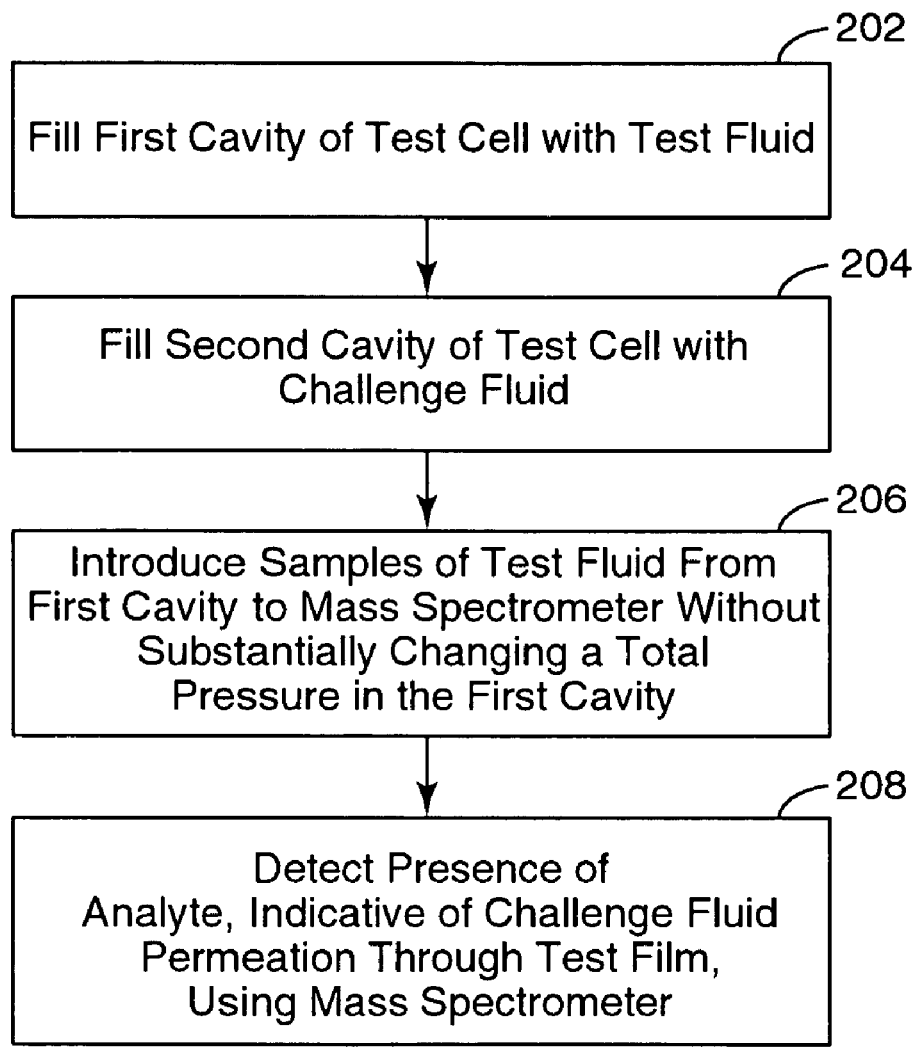
FIG. 2 is a flow diagram of a method of fluid permeation testing that may be implemented by a test apparatus in accordance with another embodiment of the present invention.

FIG. 2 illustrates a method of fluid permeation testing that may be implemented by a test apparatus in accordance with a further embodiment of the present invention. According to the illustrative example shown in FIG. 2, a first cavity of a test cell is filled 202 with a test fluid, and a second cavity of the test cell is filled 204 with a challenge fluid. The first and second cavities are preferably filled concurrently. The challenge fluid according to this embodiment comprises an inert gas, such as nitrogen, and two or more analytes.

In one approach, samples of the test fluid in the first cavity are introduced to the mass spectrometer without substantially changing the total pressure in the first cavity. In another approach, substantially balanced total pressures are maintained 206 in the first and second cavities during permeation testing, and samples of the test fluid in the first cavity are introduced 208 to a mass spectrometer.

According to one implementation, each analyte is detected 210A in a sequential manner using the mass spectrometer. According to another implementation, each analyte is detected 210B concurrently using the mass spectrometer. In both such implementations, the detected presence of each analyte is indicative of challenge fluid permeation through the test film. The rate of permeation for each analyte may be computed, and the rate of permeation of challenge fluid through the test film maybe determined 212.

Figure 3:
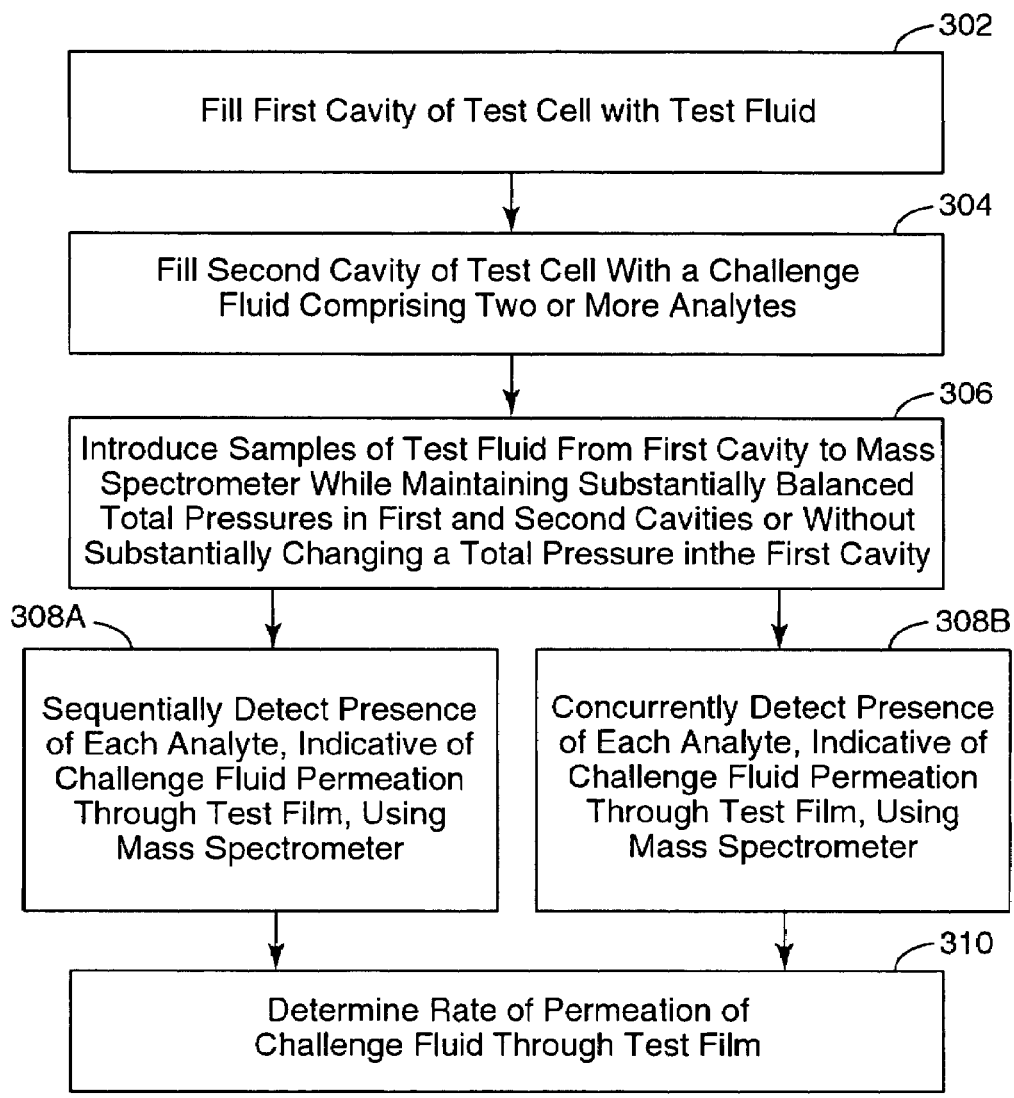
FIG. 3 is a flow diagram of a method of fluid permeation testing that may be implemented by a test apparatus in accordance with a further embodiment of the present invention.

FIG. 3 illustrates a method of fluid permeation testing that may be implemented by a test apparatus in accordance with a further embodiment. According to this method, a first cavity of a test cell is filled with a test fluid and a second cavity of the test cell is filled with a challenge fluid, shown at 302. The challenge fluid comprises an analyte. Thereafter, samples of test fluid from the first cavity are introduced to a mass spectrometer in a pulsed manner while maintaining substantially balanced pressures in the first and second cavities, shown at 304. The presence of the analyte, indicative of challenge fluid permeation through the test film, is then detected 306 using the mass spectrometer. At 310, measurements are made during all or a portion of a transitory period. The transitory period is defined between initiation of test film permeation and a time at which the test film reaches permeation equilibrium.

According to one implementation, information concerning the test film during the transitory period is then derived 312, or information concerning the test film is then derived 312 during the transitory period. According to another implementation, a time at which the test film will reach permeation equilibrium is predicted 314 based on the transitory period measurements. According to still another implementation, a permeation rate of the challenge fluid through the test film is predicted 316 based on the transitory period measurements.

The sample taken from the test cavity of the test cell may be introduced into the ionization chamber of the mass spectrometer in a pulsed fashion, such as by use of a picoliter solenoid-actuated fast sampling valve. This approach has the advantage that the analyte concentration of the test cavity of the test cell is introduced in a pulse above the internal baseline of the mass spectrometer. This approach has the further advantage that the sample volume is exceedingly small compared to the total volume of the test cavity of the test cell. For example, useful samples of the test fluid may be less than about 10 microliters. By way of further example, useful samples of the test fluid may be between 1 and 1,000 picoliters.

This means that the test cavity may be sampled frequently and for lengthy periods while leaving the test cell total pressure virtually unchanged. In general, a modest or negligible change in test cell total pressure can be tolerated during sampling as long as this change does not negatively affect the test data, such that mathematical correction or modeling would be required to correct the test data. For example, changes in the total pressure of the test cell during sampling of up to 10%, and more preferably up to 5%, in many implementations are believed to be tolerable.

Using a sampling technique according to embodiments of the present invention, the total pressures in the first and second cavities are left relatively unchanged during the sampling process. It is believed that a modest total pressure differential between the first and second cavities of no greater than about 10% is allowable during sampling of the test cavity fluid without adversely impacting the efficacy of a fluid permeation testing methodology of the present invention (i.e., does not require mathematical correction or modeling to correct the test data).

The higher total pressure within the test cavity relative to the ionization chamber of the mass spectrometer ensures a forceful pulse of test fluid into the mass spectrometer. If gas diffusion in the test cell is inadequate, a small segment of flexible nickel bellows tubing may be used with a small reciprocating cam and check valves to form a pump. Such a pump would work to force circulation from the test cavity of the test cell through a loop to the fast sampling valve and back to the test cavity to ensure adequate mixing. For oxygen as the challenge analyte, for example, diffusion alone appears adequate to equilibrate the volume of the test cavity of the test cell, and as such, a more elaborate pump apparatus need not be used.

According to alternative embodiments, aspects of the present invention may be employed in testing apparatuses where a total pressure difference exits between the challenge and test cavities of a test cell. For example, and as previously discussed, a conventional test cell implementation typically requires a relatively large differential between challenge and test cavity total pressures. Such conventional testing apparatuses may benefit from the pulsed sample injection features of the present invention, alone or in combination with the selective ion monitoring techniques described herein. Modifying a conventional testing apparatus in accordance with the present invention can provide for increased control and accuracy of permeation rate measurements.

Figure 4:
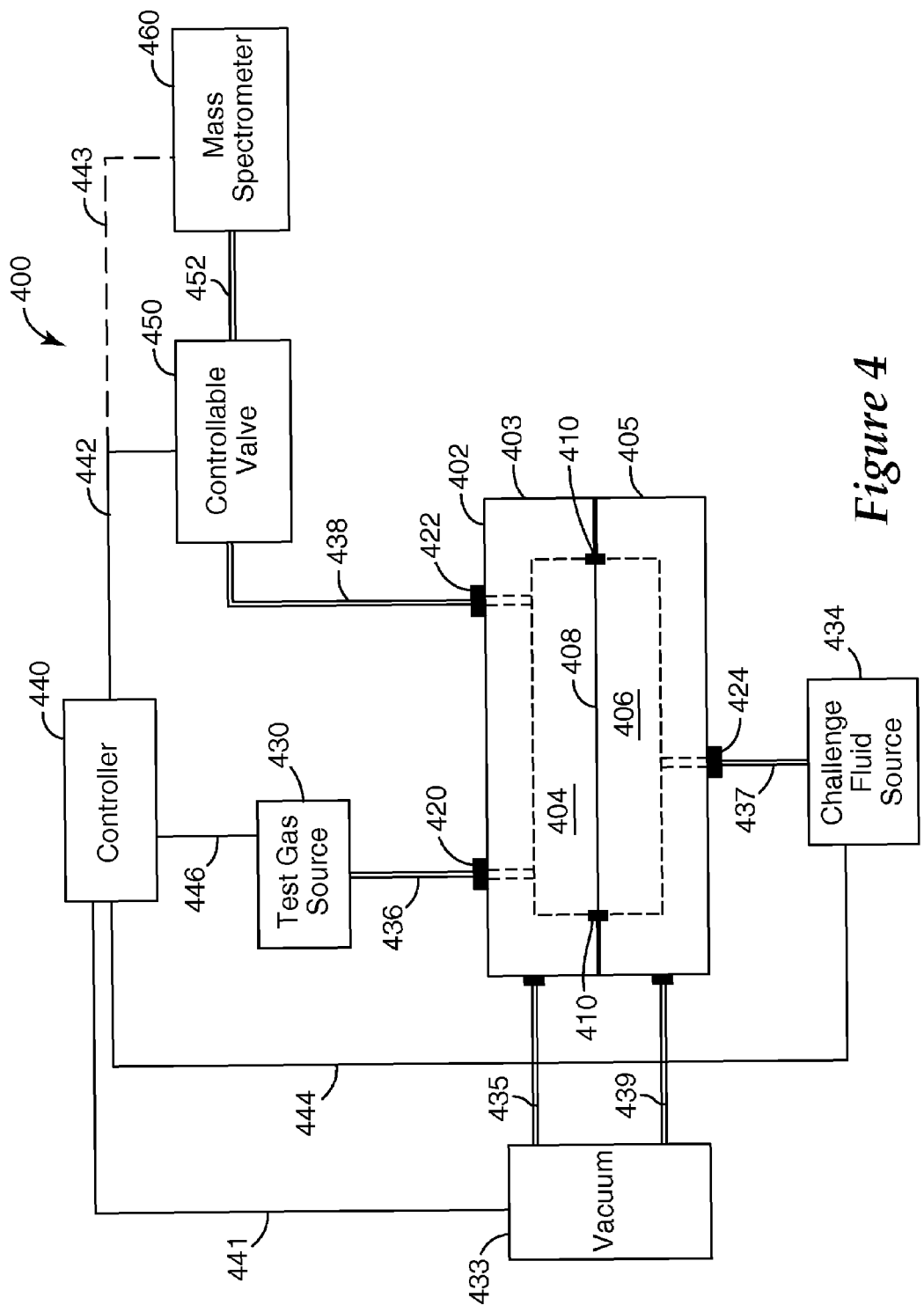
FIG. 4 is a diagram of an apparatus for testing fluid permeation of a test film in accordance with an embodiment of the present invention.

FIG. 4 is a diagram of an apparatus for testing fluid permeation of a test film in accordance with an embodiment of the present invention. The apparatus of FIG. 4 includes a test cell 402 having a first cell portion 403 and a second cell portion 405. A first cavity 404 is defined in the first cell portion 403, and a second cavity 406 is defined in the second cell portion 405.

A test film 408 is shown partitioning the first and second cavities 404, 406 of the test cell 402. The test film 408 is held suspended between first and second cavities 404, 406 of test cell 402 by a mounting arrangement 410. As will be described in greater detail, the mounting arrangement 410 and test film 408, when properly positioned within test cell 402, define a sealed partition between the first and second cavities 404, 406.

Figure 5:
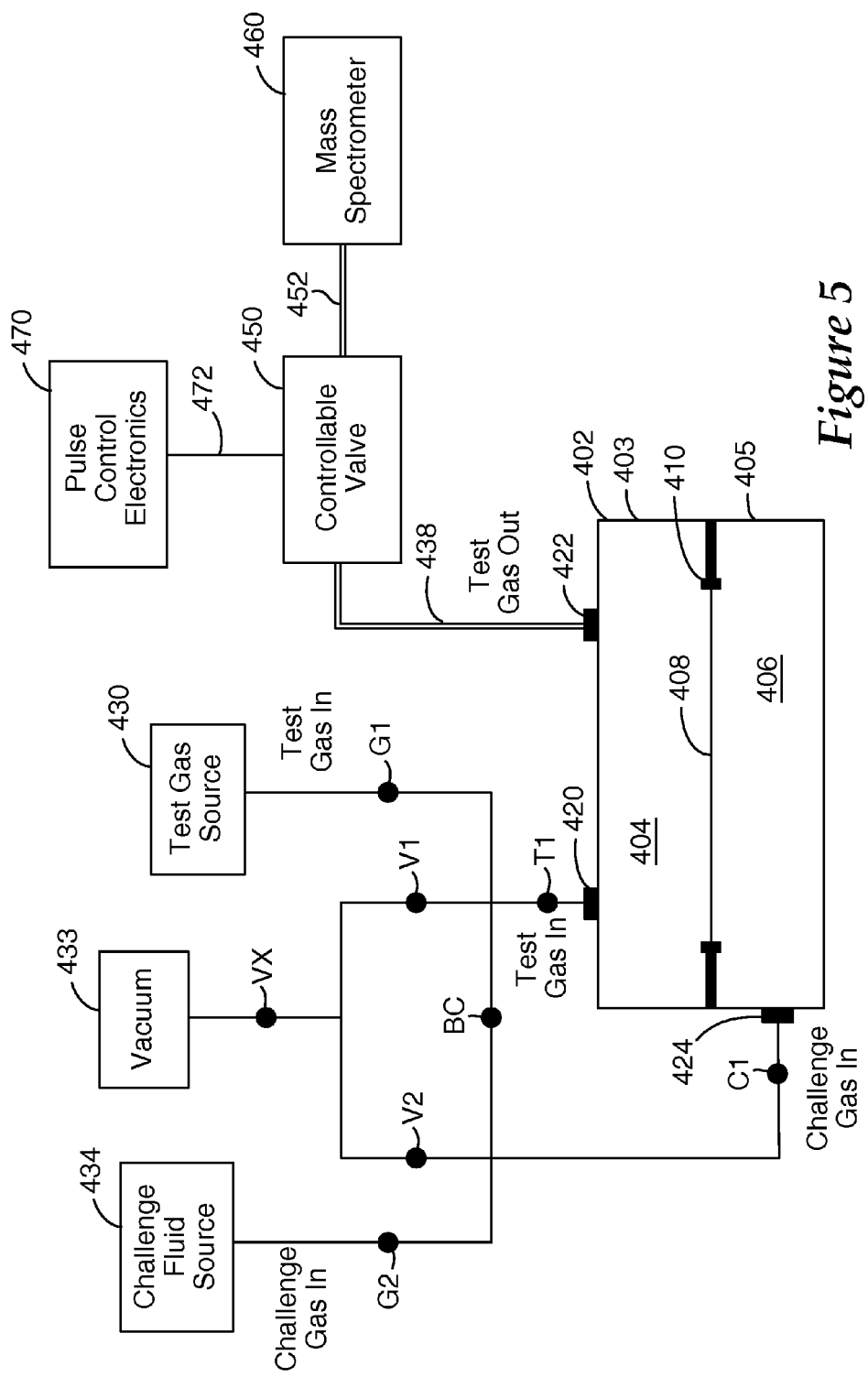
FIG. 5 is a diagram of an apparatus for testing fluid permeation of a test film in accordance with another embodiment of the present invention.

The first cavity 404 is shown to include an inlet 420 and an outlet 422. The inlet 420 of the first cavity 404 is fluidly connected to a test gas source 430 via a conduit 436. The outlet 422 of the first cavity 404 is fluidly connected to a controllable valve 450 via a conduit 438. The first and second cavities 404, 406 are also fluidly connected to a vacuum 433 via conduits 435 and 439, respectively. An alternative fluid manifold configuration is shown in FIG. 5, which is described below. The controllable valve 450 is fluidly connected to an ionization chamber of a mass spectrometer 460 via a conduit 452.

A controller 440 is coupled to the challenge fluid source 434, test gas source 430, and a vacuum 433 via control lines 444, 446, and 441 respectively. Controller 440 is also coupled to the controllable valve 450 and optionally to the mass spectrometer 460 via control lines 442 and 443, respectively. The controller 440 may be configured to control each of the challenge gas source 434, test gas source 430, vacuum 433, controllable valve 450, and mass spectrometer 460 (optionally) in a coordinated manner to implement fluid permeation testing methodologies of the present invention.

FIG. 5 is a diagram of an apparatus for testing fluid permeation of a test film in accordance with another embodiment of the present invention. The apparatus of FIG. 5 includes a test cell 402 having a similar configuration as that shown in FIG. 4. FIG. 5 shows a fluid manifold with fluid connections to the inlet or port 420 of the first cavity 404 and an inlet or port 424 of the second cavity 406. The fluid manifold includes a number of valves and conduits through which various connections may be achieved as between the first and second cavities 404, 406 and the vacuum 433, challenge fluid source 434, and test gas source 430.

Valves G1, G2, V1, V2, VX, T1, and C1 are preferably solenoid-pneumatic gas switching valves, such as model SS-4BK-TA3-16, manufactured by Swagelok, Solon, Ohio. Component BC of the fluid manifold is preferably a pressure sensor, such as an MKS BARATRON Model 223B sensor manufactured by MKS, Wilmington, Del. that may be monitored to facilitate synchronized filling and pressure balancing of the first and second cavities 404, 406 of the test cell 402. The conduits of the gas manifold may be formed from stainless steel tubing, such as ¼" diameter tubing. The conduit 438 fluidly coupling the first cavity 404 and the controllable valve 450 may be 1/16" stainless steel tubing. The conduit 452 may be a fused silica tubing.

According to one illustrative implementation, the valves of the fluid manifold shown in FIG. 5 may be controlled between open (O) and closed (C) positions during purging, filling, and measuring operations as follows:

TABLE 1

| Valve | Purge | Fill | Measure |
| --- | --- | --- | --- |
| G1 | O | O | C |
| G2 | C | O | C |
| V1 | O | C | C |
| V2 | O | C | C |
| T1 | O | O | C |
| C1 | O | O | C |
| VX | C | C | C |

According to FIG. 5, the controllable valve 450 is controlled by pulse control electronics 470. Pulse electronics 470 may be configured as a stand-alone controller or be integral or otherwise incorporated as part of a system controller, such as controller 440 shown in FIG. 4. According to one configuration, the controllable valve 450 is a picoliter solenoid-actuated fast sampling valve. A suitable controllable valve 450 is model 2020393-701 (piezoelectric valve) manufactured by Siemens Applied Automation, Bartlesville, Okla.

Pulse control electronics 470 may be implemented to include a computer-controlled high voltage pulse generator as is known in the art. According to one implementation, pulse control electronics 470 includes a computer-controlled high voltage pulse generator that provides a voltage of up to 150 volts DC and a pulse width of up to 2 milliseconds. The computer or controller of pulse control electronics 470 is preferably configured to control one or more of a pulse frequency, voltage, and pulse width of the control signal generated by the pulse electronics 470 and output to the controllable valve 450.

The controllable valve 450 is fluidly connected to the ionization chamber of mass spectrometer 460. Mass spectrometer 460 may be of varying type and configuration. A non-exhaustive, non-limiting listing of useful mass spectrometers include magnetic sector, quadrupole, time-of-flight, ion trap, and Fourier transform mass spectrometers.

Figure 6:
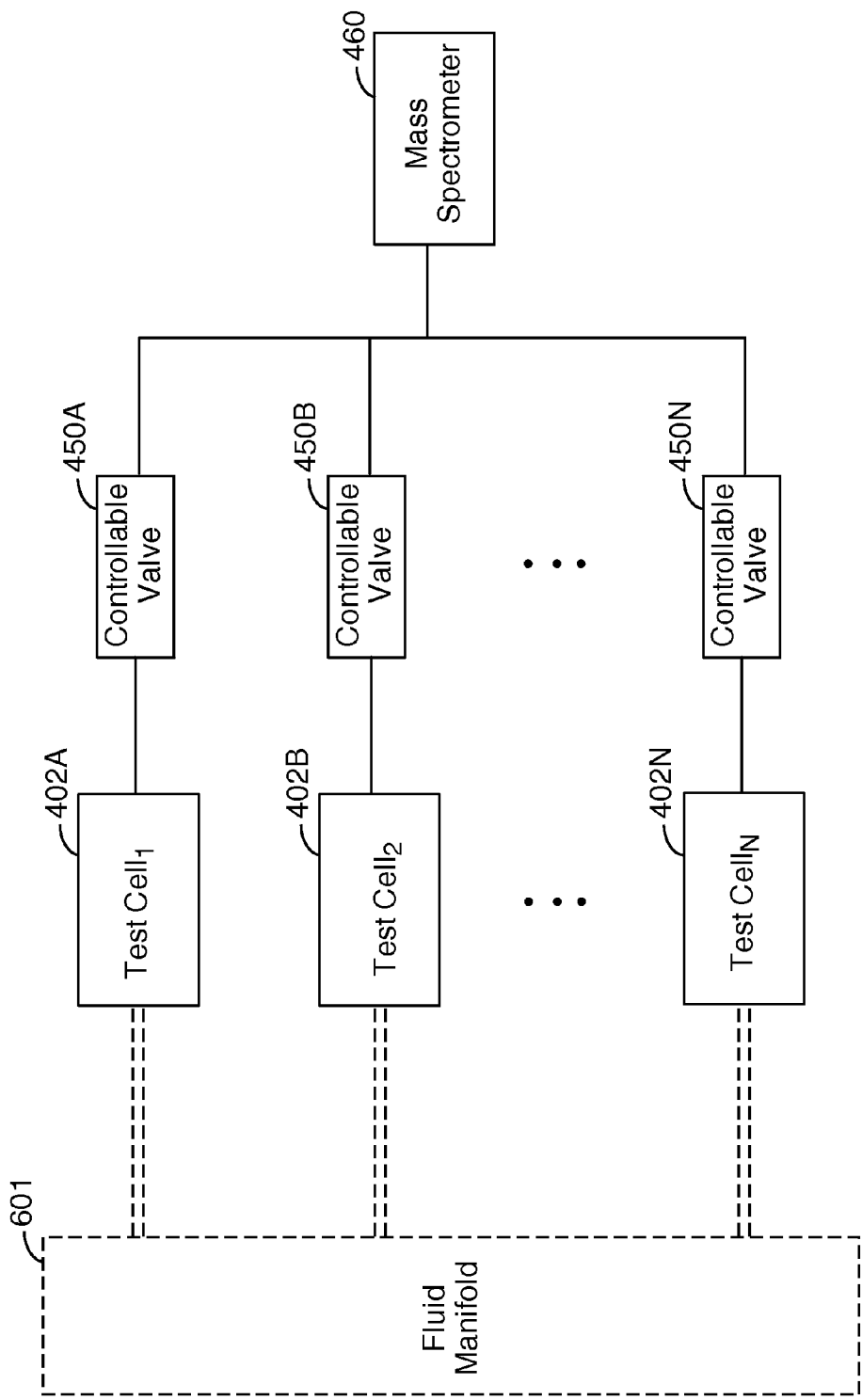
FIG. 6 is a diagram of an apparatus for testing fluid permeation of a multiplicity of test films using a common mass spectrometer in accordance with an embodiment of the present invention.

FIG. 6 is a diagram of an apparatus for testing fluid permeation of a multiplicity of test films using a common mass spectrometer in accordance with an embodiment of the present invention. The apparatus of FIG. 6 includes a number of test cells 402A, 402B, 402N, each having a configuration similar to the test cell 402 shown in FIG. 4. Each of the test cells 402A-402N is fluidly connected to a fluid manifold 601, which provides connectivity with a challenge fluid source, test fluid source, and vacuum. The fluid manifold 601 may be configured in a manner shown in FIG. 4 or FIG. 5, or be of an alternative configuration.

In the embodiment shown in FIG. 6, each of the test cells 402A-402N is fluidly connected to a controllable valve 450A-450N of a type previously described. Each of the controllable valves 450A-450N is fluidly coupled to a common mass spectrometer 460. In this manner, any number of test cells 402A-402N may be multiplexed to a common mass spectrometer 460. The test cells 402A-402N may include a challenge fluid that has one or more permeating analytes. The controllable valves 450A-450N may be controlled to selectively couple each of the test cells 402A-402N with the mass spectrometer 460, such as in a sequential fashion. Alternatively, the controllable valves 450A-450N may be controlled to selectively couple more than one test cell 402A-402N with the mass spectrometer 460. Using pulsed test fluid sample delivery and selected ion monitoring, more than one permeating analyte (in a mixture or singly) may be detected and measured, in a sequential or virtually simultaneous fashion.

Figure 7:
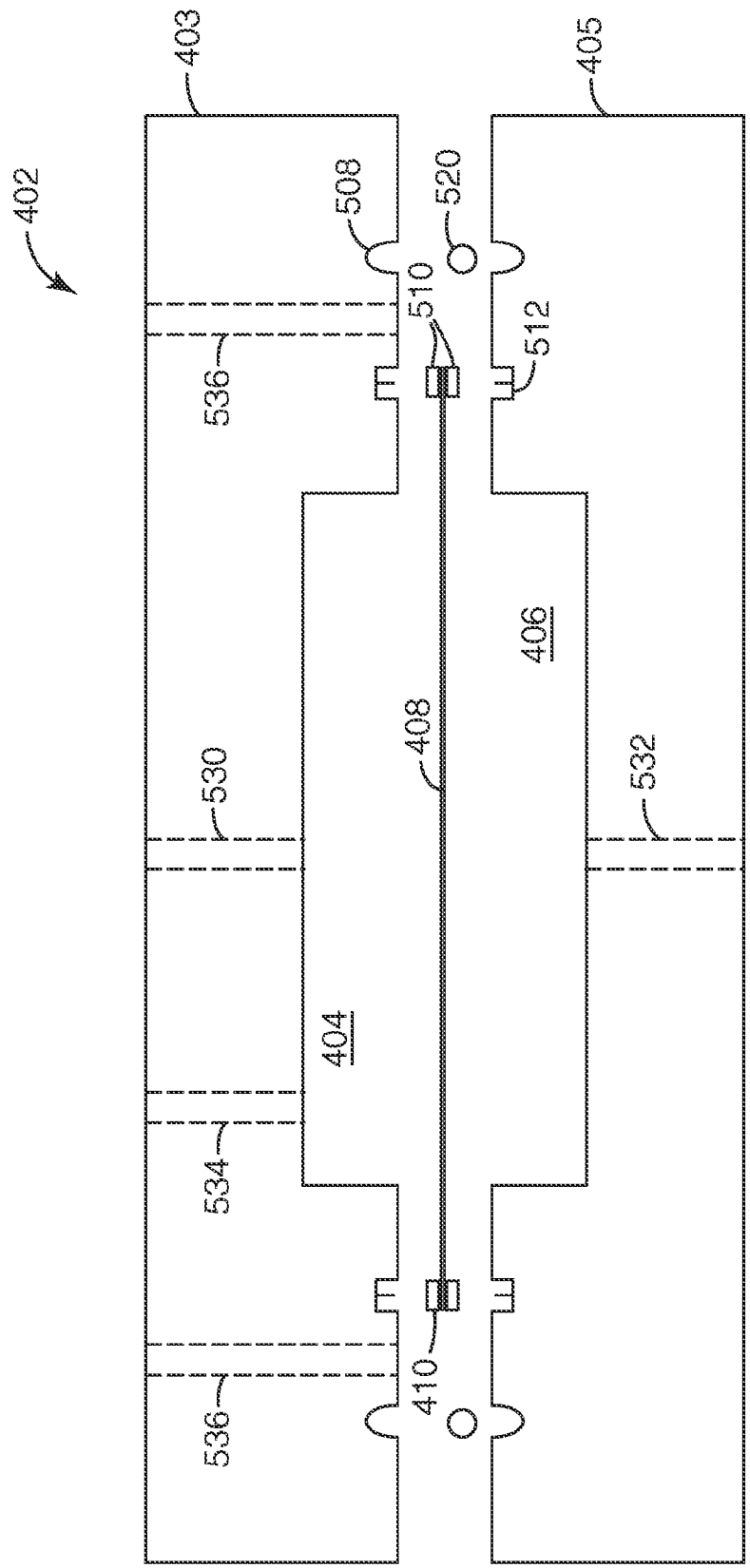
FIG. 7 is a detailed depiction of a test cell implemented in accordance with an embodiment of the present invention.

Turning now to FIG. 7, there is shown a more detailed depiction of a test cell 402 in accordance with an embodiment of the present invention. The test cell 402 includes a first cell portion 403 within which a first cavity 404 is defined. A second cell portion 405 of the test cell 402 defines a second cavity 406. In one implementation, first and second cell portions 403, 405 have a diameter of about 4 inches, and may be formed using 4-inch diameter CONFLAT blanks, model no. 600-000, available from A&N Corporation, Wiliston, Fla. Fluid channels 530 and 534 are provided in the first cavity portion 403 to facilitate communication of a test fluid into and out of the first cavity 404. A fluid channel 532 in the second cavity portion 405 facilitates communication of a challenge fluid into the second cavity 406. Fluid channels 532 and 534 may also be used for purging the first and second cavities 404 and 406.

In general, the volume of the second cavity 406, which contains the challenge fluid, is not critical. The volume of the first cavity 404, which contains the test fluid, is more critical. It is desirable that the volume of the first cavity 404 be small to enhance the relative change in analyte concentration in this volume as the analyte diffuses. However, this objective needs to be balanced against the need for a first cavity volume that is significantly greater than the volume of the controllable sampling valve (e.g., controllable valve 450 shown in FIGS. 4-6). In general, the volume relationship between the first cavity 404 (test fluid cavity), second cavity 406 (challenge fluid cavity), and sampling valve can be described as follows:

Challenge Cavity Volume>Test Cavity Volume>>Sampling Valve Volume

A test film 408 is shown suspended between first and second cavities 404, 406 of test cell 402 by a mounting arrangement 410. It is appreciated by those skilled in the art that sealing test films into a test cell of the type shown in FIG. 7 is challenging. According to one configuration, mounting arrangement 410 includes dual gaskets 510 positioned at the edges of the test film 408 on opposing sides of the test film 408. In one implementation, dual copper gaskets 510 may be used, such as CONFLAT gaskets, model no. 600-CG, available from A&N Corporation, Wiliston, Fla.

Because the asymmetry of forces acting on a single gasket 510 are balanced through the test film 408 against those acting on the matched gasket 510, this simple but effective approach has proven to work very well, thereby eliminating the need for adhesives. In an alternative configuration, an electronic grade adhesive may be used to adhere test film 408 to the gaskets 510. It may be desirable to provide a polished face or micromachined circumferential grooves on the copper gaskets 510, which may improve sealing between the gaskets 510 and the test film 408.

In one approach, CONFLAT flange bolts (not shown) may be used to provide secured engagement between the first and second cell portions 403, 405. In an alternate implementation, an over-center clamping arrangement may be used to provide the requisite mating force, which eliminates complications that may result from using flange bolts.

The first and second cell portions 403, 405 may include corresponding recesses 508 that are configured to receive an o-ring 520 or other sealing member. Additional fluid channels 536 may be provided in between the recessed channels 508 and o-ring 520 to accommodate a static pressure or a set flow of either an inert or challenge gas or some other gas which may or may not be monitored by the mass spectrometer sequence. Provision of additional channels 536 may facilitate further control of seal leaks and allow for evaluation of seal permeation of an adhesive layer placed between the copper gaskets 510 and test film 408. The annular thickness of the gaskets 510 can be varied to provide for differing path lengths in which the challenge gas would have to traverse.

The foregoing description of the various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A permeation testing apparatus, comprising:
   a mass spectrometer;
   a controllable valve comprising an inlet and an outlet, the outlet coupled to the mass spectrometer;
   a test cell comprising:
      a first cavity;
      a first port arrangement configured to facilitate fluid communication between the first cavity and a test fluid source and between the first cavity and the inlet of the controllable valve;
      a second cavity;
      a second port arrangement configured to facilitate fluid communication between the second cavity and a challenge fluid source containing a challenge fluid; and
      a support arrangement configured to suspend a test film between the first and second cavities;
   a pressure sensing arrangement configured to sense total pressures in the first and second cavities; and
   a controller coupled to the controllable valve, the controller configured to controllably actuate the valve to deliver samples of a test fluid in the first cavity to the mass spectrometer while substantially balanced total pressures are maintained in the first and second cavities.

2. The apparatus of claim 1, wherein the mass spectrometer is configured to detect presence of an analyte of the challenge fluid using a selected ion monitoring technique.

3. The apparatus of claim 1, wherein the challenge fluid comprises a plurality of analytes, and the mass spectrometer is configured to detect presence of each of the plurality of analytes.

4. The apparatus of claim 3, wherein the mass spectrometer is configured to detect the plurality of analytes in a sequential fashion or in a concurrent fashion.

5. The apparatus of claim 1, wherein an analyte of the challenge fluid comprises an isotope of an element, and the mass spectrometer is configured to detect the isotope.

6. The apparatus of claim 1, wherein the valve comprises a solenoid-actuated sampling valve.

7. The apparatus of claim 1, wherein the valve is configured to pulsedly sample a volume of less than about 10 microliters of the test fluid in the first cavity.

8. The apparatus of clam 1, wherein a processor of, or coupled to, the testing apparatus is configured to determine a rate of permeation of the challenge fluid through the test film using data produced by the mass spectrometer.

9. The apparatus of claim 1, wherein the test and challenge fluids are gases.

10. The apparatus of claim 1, wherein the challenge fluid is liquid.

11. The apparatus of claim 1, wherein the test film comprises an ultra-low permeability film.

12. The apparatus of claim 1, wherein the total pressure in each of the first and second cavities is atmospheric pressure.

13. The apparatus of claim 1, wherein the total pressures in the first and second cavities differ from one another by no greater than 10 percent.

14. The apparatus of claim 1, wherein the support arrangement comprises a gasket arrangement provided at respective ends of the test film, the gasket arrangement and test film defining a seal between the first and second cavities.

15. The apparatus of claim 14, further comprising:
   a sealing arrangement peripheral to the gasket arrangement; and
   a third port arrangement extending from a location between the sealing and gasket arrangements to an exterior surface of the test cell.

16. The apparatus of claim 14, wherein the gasket arrangement comprises metal gaskets provided above and below respective end surfaces of the test film.

17. The apparatus of claim 16, wherein the gaskets are adhesively mounted above and below the respective end surfaces of the test film.

18. A permeation testing apparatus, comprising:
   a mass spectrometer;
   a controllable valve comprising an inlet and an outlet, the outlet coupled to the mass spectrometer;
   a test cell comprising:
      a first cavity;
      a first port arrangement configured to facilitate fluid communication between the first cavity and a test fluid source and between the first cavity and the inlet of the controllable valve;
      a second cavity;
      a second port arrangement configured to facilitate fluid communication between the second cavity and a challenge fluid source containing a challenge fluid; and
      a support arrangement configured to suspend a test film between the first and second cavities;
   a pressure sensing arrangement configured to sense total pressures in the first and second cavities; and
   a controller coupled to the controllable valve, the controller configured to controllably actuate the valve to deliver samples of a test fluid in the first cavity to the mass spectrometer without substantially changing a total pressure in the first cavity.

19. The method of claim 18, wherein the total pressure in the first cavity differs from the total pressure in the second cavity.

20. The method of claim 18, wherein the total pressures in the first and second cavities are substantially balanced.

21. The apparatus of claim 18, wherein the mass spectrometer is configured to detect presence of an analyte of the challenge fluid using a selected ion monitoring technique.

22. The apparatus of claim 18, wherein an analyte of the challenge fluid comprises an isotope of an element, and the mass spectrometer is configured to detect the isotope.

23. The apparatus of claim 18, wherein the valve comprises a solenoid-actuated sampling valve.

24. The apparatus of claim 18, wherein the valve is configured to pulsedly sample a volume of less than about 10 microliters of the test fluid in the first cavity.

25. The apparatus of clam 18, wherein a processor of, or coupled to, the testing apparatus is configured to determine a rate of permeation of the challenge fluid through the test film using data produced by the mass spectrometer.

26. The apparatus of claim 18, wherein the test and challenge fluids are gases.

27. The apparatus of claim 18, wherein the challenge fluids are liquids.

28. The apparatus of claim 18, wherein the test film comprises an ultra-low permeability film.

29. The apparatus of claim 18, wherein the total pressure in each of the first and second cavities is atmospheric pressure.

30. The apparatus of claim 18, wherein the challenge fluid comprises a plurality of analytes, and the mass spectrometer is configured to detect presence of each of the plurality of analytes.

31. The apparatus of claim 30, wherein the mass spectrometer is configured to detect the plurality of analytes in a sequential fashion or in a concurrent fashion.

32. The apparatus of claim 18, wherein the support arrangement comprises a gasket arrangement provided at respective ends of the test film, the gasket arrangement and test film defining a seal between the first and second cavities.

33. The apparatus of claim 32, further comprising:
a sealing arrangement peripheral to the gasket arrangement; and
a third port arrangement extending from a location between the sealing and gasket arrangements to an exterior surface of the test cell.

34. The apparatus of claim 32, wherein the gasket arrangement comprises metal gaskets provided above and below respective end surfaces of the test film.

35. The apparatus of claim 34, wherein the gaskets are adhesively mounted above and below the respective end surfaces of the test film.

36. A permeation testing apparatus, comprising:
a mass spectrometer;
a test cell comprising a first cavity and a second cavity, the first cavity configured to contain a test fluid and the second cavity configured to contain a challenge fluid;
means for introducing samples of the test fluid in a pulsed manner from the first cavity to the mass spectrometer without substantially changing a total pressure in the first cavity; and
the mass spectrometer is configured to detect the presence of one or more analytes in the test fluid samples indicative of challenge fluid in the first cavity.

37. The apparatus of claim 36, wherein the introducing means comprises means for introducing samples of the test fluid from the first cavity to the mass spectrometer while maintaining substantially balanced total pressures in the first and second cavities.

* * * * *

UNITED STATES PATENT AND TRADEMARK OFFICE
CERTIFICATE OF CORRECTION

PATENT NO. : 7,555,934 B2  Page 1 of 1
APPLICATION NO. : 11/470766
DATED : July 7, 2009
INVENTOR(S) : Fred L. Deroos It is certified that error appears in the above-identified patent and that said Letters Patent is hereby corrected as shown below:

Column 7
Line 14, delete "maybe" and insert -- may be --, therefor.

Column 10
Lines 56-57, delete "Challenge Cavity Volume>Test cavity Volumes>>Valve Volume" and insert -- Challenge Cavity Volume$\geq$Test cavity Volumes>>Valve Volume --, therefor.

Column 13
Line 4, in Claim 19, delete "method" and insert -- apparatus --, therefor.
Line 7, in Claim 20, delete "method" and insert -- apparatus --, therefor.
Lines 28-29, in Claim 27, delete "fluids are liquids." and insert -- fluid is liquid. --, therefor.

Signed and Sealed this

Twenty-ninth Day of September, 2009

David J. Kappos
*Director of the United States Patent and Trademark Office*